United States Patent
Lindekens et al.

(10) Patent No.: US 9,109,137 B2
(45) Date of Patent: Aug. 18, 2015

(54) RADIATION CURABLE (METH) ACRYLATED COMPOUNDS

(71) Applicants: Allnex Belgium S.A., Brussels (BE); Daicel-Allnex Ltd., Tokyo (JP)

(72) Inventors: Luc Lindekens, Merchtem (BE); JoAnn Arceneaux, Marietta, GA (US); Ruben Cleymans, Halle (BE); Ichiro Nagakawa, Hiroshima (JP); Fumio Tanabiki, Hiroshima (JP); Hideo Hibiu, Hiroshima (JP)

(73) Assignees: ALLNEX BELGIUM SA, Brussels (BE); DAICEL-ALLNEX LTD, Tokyo (JP)

( * ) Notice: Subject to any disclaimer, the term of this patent is extended or adjusted under 35 U.S.C. 154(b) by 0 days.

(21) Appl. No.: 14/372,383

(22) PCT Filed: Mar. 22, 2013

(86) PCT No.: PCT/EP2013/056137
§ 371 (c)(1),
(2) Date: Jul. 15, 2014

(87) PCT Pub. No.: WO2013/144033
PCT Pub. Date: Oct. 3, 2013

(65) Prior Publication Data
US 2015/0005408 A1 Jan. 1, 2015

Related U.S. Application Data

(60) Provisional application No. 61/771,233, filed on Mar. 1, 2013, provisional application No. 61/617,870, filed on Mar. 30, 2012.

(30) Foreign Application Priority Data

Jun. 12, 2012 (EP) ..................................... 12171575

(51) Int. Cl.
| | |
|---|---|
| C07D 303/40 | (2006.01) |
| C08G 65/18 | (2006.01) |
| C08F 2/46 | (2006.01) |
| C08G 61/04 | (2006.01) |
| C09D 133/14 | (2006.01) |
| C07C 69/54 | (2006.01) |
| C07D 493/04 | (2006.01) |
| C09D 7/12 | (2006.01) |
| C08K 3/36 | (2006.01) |

(52) U.S. Cl.
CPC .............. *C09D 133/14* (2013.01); *C07C 69/54* (2013.01); *C07D 493/04* (2013.01); *C09D 7/1216* (2013.01); *C08K 3/36* (2013.01)

(58) Field of Classification Search
USPC .................. 522/170, 168, 1; 520/1
See application file for complete search history.

(56) References Cited

U.S. PATENT DOCUMENTS

| | | |
|---|---|---|
| 5,580,941 A | 12/1996 | Krause et al. |
| 5,783,616 A | 7/1998 | Krause et al. |
| 5,847,065 A | 12/1998 | Krause et al. |
| 5,854,191 A | 12/1998 | Krause et al. |
| 5,854,321 A | 12/1998 | Krause et al. |
| 7,250,209 B2 | 7/2007 | Shibahara et al. |
| 8,012,573 B2 | 9/2011 | Kowata et al. |
| 2002/0013482 A1 | 1/2002 | Brader et al. |
| 2002/0026028 A1 | 2/2002 | Epple et al. |
| 2008/0020961 A1 | 1/2008 | Rodrigues et al. |
| 2009/0018300 A1 | 1/2009 | Bloom et al. |
| 2010/0136347 A1* | 6/2010 | Simons et al. ............. 428/423.7 |
| 2011/0014139 A1* | 1/2011 | Viala et al. ....................... 424/59 |
| 2011/0046225 A1 | 2/2011 | Dalle Carbonare |
| 2011/0092718 A1 | 4/2011 | Enger et al. |
| 2011/0163267 A1 | 7/2011 | Goldfinger et al. |
| 2012/0220676 A1* | 8/2012 | Moens ......................... 521/48.5 |
| 2013/0144007 A1* | 6/2013 | Zastrow et al. ............... 524/591 |
| 2014/0073716 A1 | 3/2014 | Cho et al. |
| 2014/0249285 A1 | 9/2014 | Palmese et al. |

FOREIGN PATENT DOCUMENTS

| | | |
|---|---|---|
| CN | 1333303 | 1/2002 |
| EP | 0 648 234 | 9/1999 |
| EP | 1 881 016 | 1/2008 |
| EP | 2 226 171 | 9/2010 |
| WO | 2007/120459 | 10/2007 |
| WO | 2009/153168 | 12/2009 |
| WO | 2011/004840 | 1/2011 |
| WO | 2011/048739 | 4/2011 |
| WO | 2011/048750 | 4/2011 |
| WO | 2011/058130 | * 5/2011 |
| WO | 2011/128382 | * 10/2011 |

OTHER PUBLICATIONS

International Search Report issued Aug. 29, 2013 in International (PCT) Application No. PCT/EP2013/056125.
International Search Report issued Jun. 20, 2013 in International (PCT) Application No. PCT/EP2013/056137.

* cited by examiner

*Primary Examiner* — Ling Choi
*Assistant Examiner* — Jessica E Whiteley
(74) *Attorney, Agent, or Firm* — Wenderoth, Lind & Ponack, L.L.P.

(57) ABSTRACT

The present invention relates to (meth)acrylated compounds (A) prepared from (a) at least one cyclic ether polyol, (b) at least one linking compound (b1) and/or (b2), wherein the linking compound (b1) is selected from cyclic compounds (b11) containing at least one (I) group in the cycle where X=O or NH, from hydroxy acids (b12) and/or from alkylene oxides (b13) containing from 2 to 4 carbon atoms and the linking compound (b2) is selected from epihalohydrins or polyisocyanates, (c) a (meth)acrylating compound; and to their use in radiation curable compositions for the coatings, inks, overprint varnishes, adhesives and composites.

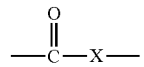

21 Claims, No Drawings

RADIATION CURABLE (METH) ACRYLATED COMPOUNDS

BACKGROUND OF THE INVENTION

Radiation curable (meth)acrylated compounds may be produced commercially from petrochemical sources. The world's supply of petroleum is being depleted and eventually the demand for petrochemical derived products may outstrip the available supply. As a consequence, the market price of petroleum and petroleum derived products would increase making them less desirable.

Biology offers an attractive alternative for industrial manufacturers looking to reduce or replace their reliance on petroleum and petrochemical derived products. The replacement of petrochemicals and petrochemical derived products with products or feedstock derived from biological resources (bio-derived products) may offer many advantages. Products and feedstock from biological sources are renewable, it may also be a response to the increasing demand for environmentally friendly products and to the price increase of petrochemical derived products.

Bioderived cyclic ether polyols obtained from various crops present a unique chemical structure that could fulfill the need for safer and more sustainable radiation curable resins. The non-aromatic cyclic structure of these derivatives provides high tensile modulus and high glass transition temperature.

The preparation of cyclic ester polyols from biological feedstock such as corn, wheat or cellulose is known and some acrylates made from these have already been described in several publications.

However, the known acrylate derivatives of bioderived cyclic ester polyols are limited to the direct acrylation of the polyols or of their alkoxylated derivatives.

US 2009/0018300 discloses several bioderived polyols and their acrylate derivatives, which are used as building blocks for the synthesis of polymers.

WO 2011/048739 and WO 2011/048750 disclose the acrylate derivative of isosorbide and radiation curable compositions thereof. These products and compositions show unexpected high cure speeds combined with low viscosities and acceptable ink or coating properties.

Few other acrylate derivatives of cyclic ether polyols are described in the art. WO 2009/153168, WO 2007/120459 and US 2002/0013482 describe aromatic (meth)acrylated derivatives of cyclic ether polyols and their use as chiral compounds.

On the other hand, there is today a real market need for the development of a broad range of bioderived radiation curable (meth)acrylated compounds for use in radiation curable compositions for the coatings, inks, overprint varnishes, adhesives and composites.

SUMMARY OF THE INVENTION

Against this background we now provide,

A (meth)acrylated compound (A) prepared from:

(a) at least one cyclic ether polyol, (b) at least one linking compound (b1) and/or (b2), wherein the linking compound (b1) is selected from cyclic compounds (b11) containing at least one

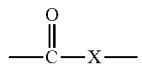

group in the cycle where X=O or NH, from hydroxy acids (b12) and/or from alkylene oxides (b13) containing from 2 to 4 carbon atoms, and wherein the linking compound (b2) is selected from epihalohydrins or polyisocyanates, (c) a (at least one) (meth)acrylating compound,
  wherein if both compounds (b1) and (b2) are being used, compound (b1) forms a moiety that links the cyclic ether polyol (a) to the linking compound (b2) which attaches to the (meth)acrylating compound (c), and
  wherein at least one compound (b2) is being used, if a compound (b13) is being used.

(Meth)acrylated compounds (A) of the invention may present one or more of the following advantages:
  they permit to achieve a fast and good curing,
  they are believed to be non-toxic,
  they may have a good solubility with other components of a UV formulation (e.g. with (meth)acrylates),
  they may have acceptable low viscosity,
  they may have glass transition temperatures within acceptable range,
  they may have low yellowing,
  they may present some resistance to oxygen inhibition,
  they permit to make radiation curable resins with a high renewable content,
  they can be used for the making of composite materials.

The present invention further discloses a process for making such (meth)acrylated compound (A).

In a further aspect of the present invention, the compositions (e.g. the coating compositions, inks, overprint varnishes, adhesives or composite matrixes) comprising (meth)acrylated compounds (A) of the present invention may present one or more of the following advantages:
  they can be used to make hard coats,
  they can be used to make coatings having improved scratch and/or abrasion resistance
  They can be used to make coatings having improved impact resistance
  they permit to achieve a more than acceptable hardness with materials having lower functionality,
  they can be used in food packaging due to their very low migration properties,
  they may have very good flow properties,
  they have high UV reactivity,
  they may have acceptable low viscosity,
  they may have low yellowing,
  they may have good mechanical properties once cured (e.g. good scratch resistance),
  they may provide excellent adhesion to for instance plastics,
  they can be cured in the presence of oxygen,
  they do not need to be formulated with bisphenol A.

Yet another aspect of the invention concerns an article or a substrate on which a composition comprising (meth)acrylated compounds (A) of the present invention is applied.

DETAILED DESCRIPTION OF THE INVENTION

In a first aspect of the invention, there is provided a (meth) acrylated compound (A) prepared from:

(a) at least one cyclic ether polyol,
(b) at least one linking compound (b1) and/or (b2), wherein the linking compound (b1) is selected from cyclic compounds (b11) containing at least one

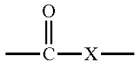

group in the cycle where X=O or NH, from hydroxy acids (b12) and/or from alkylene oxides (b13) containing from 2 to 4 carbon atoms and the linking compound (b2) is selected from epihalohydrins or polyisocyanates,
(c) a (at least one) (meth)acrylating compound,
wherein if both compounds (b1) and (b2) are being used, compound (b1) forms a moiety that links the cyclic ether polyol (a) to the linking compound (b2) which attaches to the (meth)acrylating compound (c), and wherein at least one compound (b2) is being used, if a compound (b13) is being used.

The present invention further discloses a process for making a (meth)acrylated compound (A) comprising the step of reacting:
(a) at least one cyclic ether polyol,
(b) at least one linking compound (b1) and/or (b2), wherein the linking compound (b1) is selected from cyclic compounds (b11) containing at least one

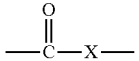

group in the cycle where X=O or NH, from hydroxy acids (b12) and/or from alkylene oxides (b13) containing from 2 to 4 carbon atoms and the linking compound (b2) is selected from epihalohydrins or polyisocyanates,
(c) at least one (meth)acrylating compound,
wherein if both compounds (b1) and (b2) are being used, compound (b1) forms a moiety that links the cyclic ether polyol (a) to the linking compound (b2) which attaches to the (meth)acrylating compound (c), and wherein at least one compound (b2) is being used, if a compound (b13) is being used.

Words importing the singular number also include the plural and vice versa unless stated otherwise.

By "(meth)acrylated" is meant to designate that compounds (A) of the invention contain one or more acryloyl groups, one or more methacryloyl groups, or a mixture of both.

By "polyols" is meant to designate organic compounds bearing two or more hydroxyl groups. Diols are often preferred.

Cyclic ether polyols (a) are compounds bearing at least one cyclic ether group and at least two hydroxyl groups. Preferred cyclic ether polyols (a) are bioderived cyclic ether polyols that are compounds derived from or synthesized by a renewable biological feedstock, such as, for example, agricultural, forestry, plant, bacterial or animal feedstock. Non exhaustive examples of such compounds are anhydrohexitols. Anhydrohexitols are obtained by dehydration of hexitols like sorbitol, mannitol, iditol, which are produced by reducing the carbonyl group of hexoses like glucose, mannose, idose that are typically derived from several biological feedstocks like wheat, corn, cellulose. The anhydrohexitols are preferably dianhydrohexitols like dianhydomannitol, dianhydrosorbitol, dianhydroiditol and mixtures thereof. The dianhydrohexitol is preferably dianhydrosorbitol, most preferably, isosorbide. A few companies have specialized in their production.

The compounds (b) according to the invention can be each independently aliphatic or aromatic compounds. Compounds (b) according to the invention are preferably aliphatic compounds. The use of aliphatic compounds (b) advantageously allows preparing (meth)acrylated compounds (A) having an improved durability especially in terms of resistance to yellowing and having a lower viscosity compared to aromatic equivalents.

By linking compound (b1) is meant to designate a compound capable of forming a moiety that links the cyclic ether polyol (a) to either the linking compound (b2) where present or to the (meth)acrylating agent (c). Compound (b1) bears at least one group reactive towards hydroxyl groups and at least one group reactive towards either the linking compound (b2) or the (meth)acrylating agent (c). This last group can be originally present on compound (b1) or be the result of the reaction of (b1) with the polyol. Compound (b1) is generally selected from cyclic compounds (b11) containing at least one

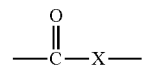

group in the cycle where X=O or NH, from hydroxy acids (such as glycolic acid) (b12) and/or from alkylene oxides (b13) containing from 2 to 4 carbon atoms. Compound (b1) is preferably an aliphatic compound.

Compound (b11) is advantageously a compound wherein X is oxygen. Compound (b11) is typically an aliphatic compound. Suitable cyclic compounds (b11) include lactones, lactams, lactides, cyclic carbonates and mixtures thereof. Particularly suitable are aliphatic lactones, lactams, lactides, cyclic carbonates and mixtures thereof. Preferred cyclic compounds (b11) are lactones, lactides and mixtures thereof. Particularly preferred lactones are ε-caprolactone, δ-valerolactone, γ-butyrolactone, and lactones of hydroxycarboxylic acids such as 2-hydroxycarboxylic acids, e.g. glycolic acid and lactic acid, 3-hydroxycarboxylic acids, e.g. 3-hydroxypropionic acid, 3-hydroxybutyric acid, 3-hydroxyvaleric acid and hydroxypivalic acid. More preferred are ε-caprolactone, δ-valerolactone, γ-butyrolactone and mixtures thereof, most preferred is ε-caprolactone. Particularly preferred lactides are L-, meso- and/or D-lactide and mixtures thereof. More preferred cyclic compounds (b11) are lactides. Lactides are advantageously bioderived lactides.

Compound (b12) is a hydroxy acid meaning a compound bearing one hydroxyl group and one carboxylic acid group. Compound (b12) may correspond to the open form of the above listed lactones. Compound (b12) is typically an aliphatic hydroxy acid. Preferred compound (b12) is glycolic acid also named hydroxyacetic acid.

Suitable compounds (b13) include ethylene oxide, propylene oxide, butylene oxide and mixtures thereof. Preferred are ethylene oxide, propylene oxide and mixtures thereof.

Linking compound (b2) is typically selected from epihalohydrins or polyisocyanates. Epihalohydrins are compounds having a halomethyl oxirane skeleton (scheme 1) wherein X is a halogen atom. Epihalohydrins are typically aliphatic compounds. Preferred epihalohydrins are epifluorohydrin, epichlorohydrin (also known as epichlorhydrin), epibromohydrin, and/or epiiodohydrin. More preferred is epichlorhydrin.

Scheme 1

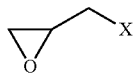

By polyisocyanate is meant to designate a compound containing at least two isocyanate groups. Typically the polyisocyanate contains not more than six isocyanate groups, more preferably not more than three isocyanate groups. Polyisocyanates may be selected from one or more aliphatic, cycloaliphatic, aromatic, heterocyclic polyisocyanates well known in the art and mixtures thereof. Examples of aliphatic and cycloaliphatic polyisocyanates that may be used are: 1,6-diisocyanatohexane (HDI), 1,1'-methylene bis[4-isocyanatocyclohexane] (H12MDI), 5-isocyanato-1-isocyanatomethyl-1,3,3-trimethylcyclohexane (isophorone diisocyanate, IPDI).

Examples of polyisocyanates containing more than two isocyanate groups are the biuret and isocyanurate derivatives of the above mentioned diisocyanates. Aliphatic polyisocyanates containing more than two isocyanate groups are for example the derivatives of above mentioned diisocyanates like 1,6-diisocyanatohexane biuret and isocyanurate.

Examples of aromatic polyisocyanates that may be used are 1,4-diisocyanatobenzene (BDI), 2,4-diisocyanatotoluene (TDI), 1,1'-methylenebis[4-isocyanatobenzene] (MDI), xylilene diisocyanate (XDI), 1,5-naphtalene diisocyanate (NDI), tolidine diisocyanate (TODI, tetramethylxylylene diisocyanate (TMXDI) and p-phenylene diisocyanate (PPDI). Other examples of polyisocyanates that may be used in the context of the invention are trimethylhexa-methylenediisocyanate, 4,4'-diisocyanatodicyclohexylmethane, 4,4'-diisocyanatodiphenylmethane, the technical mixtures with 2,4-diisocyanatodiphenylmethane and also the higher homologues of above mentioned diisocyanates, 2,4-diisocyanatotoluene and technical mixtures of them with 2,6-diisocyanatotoluene, as well as the copolymerization product of 3-isopropenyl-α,α'-dimethylbenzyl isocyanate (TMI). Preferred are aliphatic polyisocyanates.

In one variant of the present invention, the polysisocyanate is preferably a diisocyanate. The diisocyanate can be an aliphatic diisocyanate and it can be an aromatic diisocyanate.

In another variant the polysisocyanate is preferably a triisocyanate such as an isocyanurate. The triisocyanate can be an aliphatic triisocyanate and it can be an aromatic diisocyanate. The use of a triisocyanate advantageously improves the impact resistance of the formed (meth)acrylate compound (A).

In yet another variant, the polyisocyanate is a mixture of at least one diisocyanate and at least one triisocyanate. They can each independently be aliphatic polyisocyanates or aromatic polyisocyanates.

By (meth)acrylating compound (c) is meant to designate a compound comprising at least one (meth)acryloyl group and at least one group reactive towards compounds (b1) or (b2), depending on the compounds used for the preparation of the (meth)acrylated compound (A), or towards their reaction products with the cyclic ether polyol (a). Typically (meth) acrylating compounds (c) are selected from compounds (c1) and/or from compounds (c2).

Compounds (c1) are selected from an unsaturated acid and/or a suitable equivalent thereof. Examples of suitable equivalents are for instance the acyl halide of the unsaturated acid, the corresponding anhydride of the unsaturated acid and/or a lower alkyl ester of the unsaturated acid. With lower alkyl is meant a $C_1$-$C_4$ alkyl. Particularly suited for use in the present invention are (meth)acrylic acid, (meth)acrylic acid anhydride, a (meth)acrylic acid halide, and/or a lower alkyl ester of (meth)acrylic acid. Examples of suitable (meth) acrylic acid halides are (meth)acrylic acid chloride, (meth) acrylic acid bromide and/or (meth)acrylic acid iodide. By a lower alkyl ester is meant to designate in particular the lower alcohol ester of an unsaturated acid such as (meth)acrylic acid. The lower alcohol preferably is an aliphatic $C_1$-$C_4$ alcohol. Preferred lower alkyl esters are for instance methyl esters, ethyl esters, n-propyl esters and/or iso-propyl esters of (meth)acrylic acid. When a (meth)acrylic acid halide is used and/or (meth)acrylic acid anhydride, it is desirable to work in anhydrous conditions to avoid compounds hydrolysis. Preferred for use in the invention are unsaturated monoacids. A most preferred compound (c1) is (meth)acrylic acid.

Compounds (c2) are compounds that contain at least one reactive group capable to react with isocyanate groups as well as at least one (meth)acryloyl group. Typically compounds (c2) are compounds that contain at least one (meth)acryoyl group and one (or essentially one) nucleophilic function capable of reacting with isocyanate groups, such as a hydroxyl group. Other possible groups are amino and/or thiol groups. Hydroxyl groups though are preferred. Useful compounds (c2) include the esterification products of aliphatic and/or aromatic polyols with (meth)acrylic acid having a residual average hydroxyl functionality of about 1. Mono (meth)acryloyl mono-hydroxy compounds as well as poly (meth)acryloyl mono-hydroxy compounds can be used.

Preferred mono(meth)acryloyl mono-hydroxy compounds are hydroxymethyl (meth)acrylate, hydroxyethyl (meth) acrylate, hydroxypropyl (meth)acrylate and/or hydroxybutyl (meth)acrylate. More preferred are the acrylate derivatives.

Poly(meth)acryloyl mono-hydroxy compounds are typically the partial esterification products of (meth)acrylic acid with tri-, tetra-, penta- or hexahydric polyols or mixtures thereof. It is known to those skilled in the art that the partial (meth)acrylation of such polyols proceeds to a mixture of products bearing from one to six (meth)acrylate groups and that a possible way to characterize the mixture is by measuring its hydroxyl value. In the present case, the hydroxyl value is such that the residual average hydroxyl functionality of the mixture is one (or essentially one). Preferred examples of poly(meth)acryloyl mono-hydroxy compounds are compounds comprising at least two (meth)acryl functions such as glycerol di(meth)acrylate, trimethylolpropane di(meth)acrylate, glycerol di(meth)acrylate, pentaerythritol tri(meth)acrylate, ditrimethylolpropane tri(meth)acrylate, dipentaerythritol penta(meth)acrylate and their (poly)ethoxylated and/or (poly)propoxylated equivalents. More preferred poly(meth) acryloyl mono-hydroxy compounds are glycerol di(meth) acrylate, trimethylolpropane di(meth)acrylate. Another more preferred poly(meth)acryloyl mono-hydroxy compound is pentaerythritol tri(meth)acrylate.

Most preferred are the acrylate derivatives.

In this context, it is also possible to use reaction products of such polyols with ethylene oxide, propylene oxide and/or lactones, which add to these polyols in a ring-opening reaction. Examples of suitable lactones are ε-caprolactone, δ-valerolactone, γ-butyrolactone. Glycolides and lactides can be used for the same purpose. These modified or unmodified polyols are partly esterified with acrylic acid, methacrylic acid or mixtures thereof until the desired residual hydroxyl functionality is reached. Examples of useful compounds in this category are Tone M100 (Dow Chemicals), Bisomer PEMCURE 12A (Cognis) and/or the reaction products (or adducts) of a (meth)acryloyl hydroxy compound and for instance Galacid Slow release (GALACTIC SA), FUTERRO® Lactide LF (Futerro), PURALACT® L, PURALACT® D or PURASORB® G (Purac), or mixtures of these (of any of these).

Compounds (c2) obtained from the reaction of (meth) acrylic acid with aliphatic, cycloaliphatic or aromatic compounds bearing an epoxy functionality, forming a compound bearing a hydroxyl functionality together with at least one (meth)acrylic functionality can be used as well.

Most preferred compounds (c2) are hydroxyethylacrylate, glycerol diacrylate, trimethylolpropane diacrylate and mixtures thereof. Another most preferred compound (c2) is pentaerythritol triacrylate.

In a particular variant of the present invention, a mixture of mono(meth)acryloyl mono-hydroxy compounds and of poly (meth)acryloyl mono-hydroxy compounds can also be used. Mixtures of acrylate derivatives are preferred such as a mixture of hydroxyethylacrylate and pentaerythritol triacrylate "PETIA" (mixture of tri- and tetra-acrylate).

In a first mode of execution of the present invention, at least one linking compound (b2) is present. In particular, there is provided a (meth)acrylated compound (A) prepared from:
 (a) at least one cyclic ether polyol,
 (b) at least one linking compound (b2) selected from epihalohydrins or polyisocyanates and optionally at least one linking compound (b1) selected from cyclic compounds (b11) containing at least one

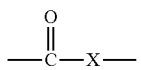

group in the cycle where X=O or NH, from hydroxy acids (b12) and/or from alkylene oxides (b13) containing from 2 to 4 carbon atoms,
 (c) a (at least one) (meth)acrylating compound, wherein if both compounds (b1) and (b2) are being used, compound (b1) forms a moiety that links the cyclic ether polyol (a) to the linking compound (b2) which attaches to the (meth)acrylating compound (c).

In a first embodiment of the first mode of execution of the present invention, the (meth)acrylated compound (A) is prepared from a cyclic ether polyol (a), a linking compound (b2) selected from epihalohydrins and a (meth)acrylating compound (c1) selected from unsaturated acids. In this first embodiment, the compound (b2) links the cyclic ether polyol (a) to the (meth)acrylating compound (c1). Compound (A) according to this first embodiment can be prepared in different ways. The compound (A) may for instance be prepared by a process comprising a first step wherein the cyclic ether polyol is reacted with the epihalohydrin to form a product having one or more epoxy groups, and a second step comprising the reaction of the product obtained in the first step with one or more suitable (meth)acrylating compounds. The reaction is generally conducted under heat and in the presence of one or more catalysts. Although solvent is not required, it may be used to facilitate the heat and mass transfer and one or more polymerization inhibitors may be added during or after the reaction. Depending on the reaction conditions and reaction stoichiometry, the reaction of the cyclic ether polyol (a) with the linking compound (b2) can lead to an extended structure comprising the repetition of (a)-(b2) links and terminated by epoxy groups. However, the preferred structures are not extended. After reaction with the (meth)acrylating compound (c1), the preferred (meth)acrylated compound (A) contains essentially no residual epoxy group. Typically, the (meth)acrylated compound (A) has a residual epoxy value below 0.1 milliequivalent per gram of compound (A).

In a second embodiment of the first mode of execution of the present invention, the (meth)acrylated compound (A) is prepared from a cyclic ether polyol (a), a linking compound (b2) selected from polyisocyanates, a (meth)acrylating compound selected from (c2) compounds. In this second embodiment, the compound (b2) links the cyclic ether polyol (a) to the (meth)acrylating compound (c2). Compound (A) according to this second embodiment can be produced in many ways. For example, compounds (a), (b2) and (c2) may be reacted together at once. Alternatively, compound (A) may be made by pre-reacting a polyisocyanate (b2) with a (meth) acrylating compound (c2) to form an adduct with at least one free isocyanate group, which is later reacted with a cyclic ether polyol (a); or a cyclic ether polyol (a) and polyisocyanate (b2) may be reacted first and this product reacted further with a (meth)acrylating compound (c2). The reaction is generally conducted under heat and in the presence of one or more catalysts. Although solvent is not required, it may be used to facilitate the heat and mass transfer and one or more polymerization inhibitors may be added during or after the reaction. Depending on the reaction conditions and reaction stoichiometry, the reaction of the cyclic ether polyol (a) with the linking compound (b2) can lead to an extended structure comprising the repetition of (a)-(b2) links and terminated by isocyanate groups. However, the preferred structures are not extended.

After reaction with the (meth)acrylating compound (c2), the preferred (meth)acrylated compound (A) contains essentially no residual isocyanate group. Typically, the (meth)acrylated compound (A) has a residual isocyanate value below 0.2% NCO.

In a variant of these two first embodiments, at least one linking compound (b1) is further used for the preparation of the (meth)acrylated compound (A). In one embodiment of this variant, the at least one linking compound (b1) is an aliphatic compound. In another embodiment, it is an aromatic compound. In yet another embodiment, it is a mixture of aliphatic and aromatic compounds. Preferably, the at least one linking compound (b1) is aliphatic. In this variant, the (meth)acrylated compound (A) is prepared from a cyclic ether polyol (a), a linking compound (b1), a linking compound (b2) and a (meth)acrylating compound (c). The linking compound (b1) is typically selected from compounds (b11), from (b12) and/or from (b13), preferably from (b11) compounds. Preferred compounds (b11) are selected from lactones, lactams, lactides, cyclic carbonates and mixtures thereof, more preferred compounds (b11) are selected from lactones and lactides and mixtures thereof, most preferred are selected from lactides. In this variant, compound (b1) forms a moiety that links the cyclic ether polyol (a) to the linking compound (b2) that also links to the (meth)acrylating compound (c) in a sequence:
 (a)*-(b1)*-(b2)*-(c)*, wherein
 (a)*, (b2)* and (c)* are residues of respectively (a), (b2) and (c)
 (b1)* is a moiety formed from (b1).

Compound (b1) has typically at least one group reactive towards hydroxyl groups and at least one group reactive towards the linking compound (b2). This last group can be originally present on compound (b1) or be the result of the reaction of (b1) with the polyol. Typically, when a compound (b11) is used, the reaction is a ring opening reaction. The reactions between (a) and (b1) and between (b1) and (b2) can be conducted according to any suitable method. For instance, an adduct between the cyclic ether polyol (a) and the linking compound (b1) may first be formed followed by the reaction with compound (b2) and compound (c). These steps are generally conducted under heat and in the presence of one or more catalysts. Although solvent is not required, it may be used to facilitate the heat and mass transfer and one or more polymerization inhibitors may be added during or after the reaction. As will be apparent to the skilled person, depending on the equivalent ratio of compound (b1) to the hydroxyl groups of the cyclic ether polyol (a) and on the reaction conditions, some oligomerization or polymerization of compound (b1) can take place. The number of repeating units of the moiety (b1)* of the adduct is generally from 1 to 10, preferably from 1 to 5, more preferably from 1 to 2. These units are randomly spread over the hydroxyl groups of the cyclic ether polyol (a).

In the first embodiment of the present invention and the variant of this first embodiment, typically the amounts of compounds (a), (b2), (c1) and optionally (b1) sum up to 100%.

In the second embodiment of the present invention and the variant of this second embodiment, typically the amounts of compounds (a), (b2), (c2) and optionally (b1) sum up to 100%.

In a second mode of execution of the present invention, at least one aliphatic linking compound (b1) is present. In particular, there is provided a (meth)acrylated compound (A) prepared from:
(a) at least one cyclic ether polyol,
(b) at least one aliphatic linking compound (b1) selected from cyclic compounds (b11) containing at least one

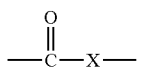

group in the cycle where X=O or NH, from hydroxy acids (b12) and/or from alkylene oxides (b13) containing from 2 to 4 carbon atoms, optionally at least one linking compound (b2) selected from epihalohydrins or polyisocyanates,
(c) a (at least one) (meth)acrylating compound
wherein if both compounds (b1) and (b2) are being used, compound (b1) forms a moiety that links the cyclic ether polyol (a) to the linking compound (b2) which attaches to the (meth)acrylating compound (c), and
wherein at least one compound (b2) is being used, if a compound (b13) is being used.

In a third embodiment of the present invention according to the second mode of execution, the (meth)acrylated compound (A) is prepared from a cyclic ether polyol (a), an aliphatic linking compound (b1) selected from compounds (b11) and/or from compounds (b12) and a (meth)acrylating compound (c1) selected from unsaturated acids and/or suitable equivalents thereof. Compounds (b11) and compounds (b12) are preferably aliphatic compounds. In this third embodiment, the compound (b1) links the cyclic ether polyol (a) to the (meth)acrylating compound (c1). Compound (A) according to this second embodiment can be produced in many ways. The compound (A) may for instance be prepared by a process comprising a first step wherein the cyclic ether polyol is reacted with the linking compound (b1) selected from (b11) and/or (b12) as described in the variant supra to form an adduct, and a second step comprising the reaction of the adduct obtained in the first step with one or more suitable (meth)acrylating compounds (c1). The reaction is generally conducted under heat and in the presence of one or more catalysts. Although solvent is not required, it may be used to facilitate the heat and mass transfer and one or more polymerization inhibitors may be added during or after the reaction. In this embodiment, the number of repeating units of the formed moiety (b1)* of the adduct is generally from 1 to 10, preferably from 1 to 5, more preferably from 1 to 2. Preferred linking compounds (b1) of this embodiment are selected from (b11) compounds, more preferably from lactones, lactams, lactides, cyclic carbonates and mixtures thereof, most preferably from lactones and lactides and mixtures thereof.

In this third embodiment of the present invention, typically the amounts of compounds (a), (b11) and/or (b12) and (c1) sum up to 100%.

In a fourth embodiment of the present invention according to the second mode of execution, the (meth)acrylated compound (A) is prepared from a cyclic ether polyol (a), an aliphatic linking compound (b1), a linking compound (b2) and a (meth)acrylating compound (c). The linking compound (b1) is typically selected from compounds (b11), from (b12) and/or from (b13), preferably from (b11) compounds. Preferred compounds (b11) are selected from lactones, lactams, lactides, cyclic carbonates and mixtures thereof, more preferred compounds (b11) are selected from lactones and lactides and mixtures thereof, most preferred are selected from lactides. In a variant of this embodiment, the linking compound (b2) is an aliphatic compound. In another variant, it is an aromatic compound. In yet another variant, it is a mixture of aliphatic and aromatic compounds.

In this embodiment, compound (b1) forms a moiety that links the cyclic ether polyol (a) to the linking compound (b2) that also links to the (meth)acrylating compound (c) in the above described sequence.

Compound (b1) has typically at least one group reactive towards hydroxyl groups and at least one group reactive towards the linking compound (b2). This last group can be originally present on compound (b1) or be the result of the reaction of (b1) with the polyol. Typically, when a compound (b11) is used, the reaction is a ring opening reaction. The reactions between (a) and (b1) and between (b1) and (b2) can be conducted according to any suitable method. For instance, an adduct between the cyclic ether polyol (a) and the linking compound (b1) may first be formed followed by the reaction with compound (b2) and compound (c). These steps are generally conducted under heat and in the presence of one or more catalysts. Although solvent is not required, it may be used to facilitate the heat and mass transfer and one or more polymerization inhibitors may be added during or after the reaction. As will be apparent to the skilled person, depending on the equivalent ratio of compound (b1) to the hydroxyl groups of the cyclic ether polyol (a) and on the reaction conditions, some oligomerization or polymerization of compound (b1) can take place. The number of repeating units of the moiety (b1)* of the adduct is generally from 1 to 10, preferably from 1 to 5, more preferably from 1 to 2. These units are randomly spread over the hydroxyl groups of the cyclic ether polyol (a).

In this fourth embodiment, typically the amounts of compounds (a), (b1), (b2) and (c) sum up to 100%.

In a first variant of this fourth embodiment, the linking compound (b2) is selected from epihalohydrins and the (meth)acrylating compound (c) is selected from unsaturated acids. After reaction with the (meth)acrylating compound (c), the preferred (meth)acrylated compound (A) contains essentially no residual epoxy group. Typically, the (meth)acrylated compound (A) has a residual epoxy value below 0.1 milliequivalent per gram of compound (A).

In a second variant of this fourth embodiment, the linking compound (b2) is selected from polyisocyanates and the (meth)acrylating compound (c) is selected from (c2) compounds. After reaction with the (meth)acrylating compound (c), the preferred (meth)acrylated compound (A) contains essentially no residual isocyanate group. Typically, the (meth)acrylated compound (A) has a residual isocyanate value below 0.2% NCO.

Generally, the (meth)acrylated compounds (A) according to the invention are prepared in the absence of solvent.

In a variant according to the present invention, a solvent can be used for the preparation of the (meth)acrylated compound (A) to facilitate the heat and mass transfer. It is generally used in an amount from 5% by weight to 90% by weight. The amount of solvent is preferably at least 10% by weight, more preferably at least 15% by weight. The amount of solvent is preferably at most 60% by weight, more preferably at most 30% by weight. The % by weight are based on the total weight of the solvent and compounds (a), (b) and (c).

Examples of solvents suitable for use are ethyl acetate, butyl acetate, isobutyl acetate, acetone, methyl ethyl ketone (MEK), methyl isobutyl ketone (MIBK), diisobutyl ketone, diethylene glycol monobutyl ether acetate, and propylene glycol monomethyl acetate. Preferred solvent is methyl ethyl ketone (MEK).

(Meth)acrylated compounds (A) according to the invention have typically an average (meth)acrylate functionality of at least 2 expressed as the number of (meth)acrylate groups per molecule of (meth)acrylated compound (A). (Meth)acrylated compounds (A) according to the invention have typically an average (meth)acrylate functionality of at most 20, preferably the average functionality does not exceed 16, more preferably it does not exceed 12. An average functionality of 2 gives (meth)acrylated compounds (A) having a good scratch and/or abrasion resistance. A higher functionality leads to an improved scratch and/or abrasion resistance.

Preferred compounds (A) according to the invention are preferably acrylated compounds (A).

Typically (meth)acrylated compounds (A) of the invention have a molecular weight (MW) of from 200 to 2000 Daltons as theoretically calculated on the basis of the reagents amounts used. More typically the molecular weight is at least 250 Daltons, more preferably at least 300 Daltons. In general the molecular weight is at most 1500 Daltons, more preferably at most 1000 Daltons. Typically, the molecular weight is at most 1400 Daltons, more preferably at most 1300 Daltons. The molecular weights are number average molecular weights.

Preferably (meth)acrylated compounds (A) of the invention have a viscosity as measured at 25° C. ranging from 800 to 40,000 mPa·s. Typically the viscosity is at most 25,000 mPa·s, more preferably at most 10,000 mPa·s.

In the particular variant of the invention wherein the (meth)acrylated compound (A) is prepared in the presence of a solvent, the (meth)acrylated compound (A) has typically a MW of from 500 to 200,000 Daltons. More typically the molecular weight is at least 800 Daltons, more preferably at least 1000 Daltons. In general the molecular weight is at most 150,000 Daltons, more preferably at most 100,000 Daltons. The molecular weights are number average molecular weights.

In this variant, (meth)acrylated compounds (A) of the invention have typically a viscosity as measured at 25° C. ranging from 1 to 100,000 mPa·s. Typically the viscosity is at most 80,000 mPa·s, more preferably at most 50,000 mPa·s.

An advantage of (meth)acrylated compounds (A) of the invention is their high cure speed. Compounds (A) of the invention are highly suitable for use in coating compositions. Coating compositions can be clear (e.g. lacquers) or pigmented. Compounds (A) of the invention are particularly suited for the preparation of hard coats.

Compounds (A) of the invention are further also suitable for use in inks, varnishes and adhesives. (Meth)acrylated compounds (A) of the invention are also suitable for use in matrixes for composites (clear or pigmented). They are further suited for use in stereolithography applications.

The present invention allows to make (meth)acrylated compounds (A) with high renewable content. For instance compounds (A) can be prepared wherein at least 1% by weight of the carbon content of the compound is from renewable materials, relative to the total weight of compound (A). Typically this amount is at least 2% by weight, more preferably at least 5% by weight. The natural derived carbon content can even be as high as 10% or even more.

A second aspect of the invention relates to a radiation curable composition comprising at least one (meth)acrylated compound (A) of the invention.

Typically compositions of the invention comprise, relative to the total weight of the organic non-volatile content of the composition, at least 5%, by weight, of (meth)acrylated compounds (A) of the invention. Typically this amount is at least 20%, more typically at least 50%, by weight. Typically this amount is at most 90%, more typically at most 70%, by weight.

Often, the compositions of the invention further comprise at least one compound (B) which is different from compounds (A). Compound (B) typically is a reactive diluting monomer. Compound (B) typically contains at least one active energy ray curable group, more in particular at least one (meth)acryloyl group, allyl group and/or vinyl group. Most typical are (meth)acryloyl groups.

Typically compositions of the invention comprise, relative to the total weight of the organic non-volatile content of the composition, from 0 to 90% by weight, more in particular from 5 to 60% by weight of compounds (B). Where present, they are typically present in an amount of at least 10% by weight, more typically at least 20% by weight, relative to the total weight of the organic non-volatile content of the composition. Typically this amount is at most 80% by weight, more typically at most 70% by weight.

Suitable monomers (B) are mono and poly(meth)acrylated monomers. Examples of such monomers (B) are butyl(meth)acrylate, methyl(meth)acrylate, isobutyl(meth)acrylate, 2-ethylhexyl(meth)acrylate, cyclohexyl(meth)acrylate, n-hexyl(meth)acrylate, isobornyl(meth)acrylate, iso-octyl (meth)acrylate, n-lauryl(meth)acrylate, octyl/decyl(meth)acrylate, 2-hydroxyethyl(meth)acrylate, phenoxyethyl (meth)acrylate, nonylphenolethoxylate mono(meth)acrylate, 2-(-2-ethoxyethoxy)ethyl(meth)acrylate, 2-butoxyethyl (meth)acrylate, 1,6-hexanediol di(meth)acrylate (HDD(M)A), di or tri propylene glycol di(meth)acrylate (DPGD(M)A, TPGD(M)A), ethoxylated and/or propoxylated neopentylglycol di(meth)acrylate, pentaerythritol tri(meth)acrylate (PETI(M)A) and the ethoxylated and/or propoxylated derivatives thereof, trimethylolpropane tri(meth)acrylate (TMPT (M)A) and the ethoxylated and/or propoxylated derivatives thereof, di-trimethylolpropane tri(meth)acrylate (diTMPT (M)A) glycerol tri(meth)acrylate and the ethoxylated and/or propoxylated derivatives thereof, dianhydrohexitols di(meth)acrylates (like isosorbide di(meth)acrylate) and the ethoxylated and/or propoxylated derivatives thereof, bisphenol A di(meth)acrylate and the ethoxylated and/or propoxylated derivatives thereof, phenylglycidylether(meth)acrylate and the ethoxylated or/and propoxylated derivatives thereof, the (meth)acrylates obtained from the esterification with (meth) acrylic acid of aliphatic glycidyl ethers, especially those wherein the alkyl chain comprises from 6 to 24 carbon atoms, more preferably from 8 to 18 carbon atoms, and/or of glycidyl esters of saturated and unsaturated carboxylic acids, especially the glycidyl esters of long chain alkyl carboxylic acids wherein the alkyl chain comprises from 6 to 24 carbon atoms, more preferably from 8 to 18 carbon atoms.

Preferred monomers (B) are di and tri(meth)acrylated monomers such as 1,6-hexanediol di(meth)acrylate (HDD(M)A), di or tri propylene glycol di(meth)acrylate (DPGD(M)A, TPGD(M)A), trimethylolpropanetri(meth)acrylate (TMPT(M)A) and the ethoxylated and/or propoxylated derivatives thereof, pentaerythritoltri(meth)acrylate (PETI(M)A) and the ethoxylated and/or propoxylated derivatives thereof, glyceroltri(meth)acrylate and the ethoxylated and/or propoxylated derivatives thereof, dianhydrohexitols di(meth) acrylates (like isosorbide di(meth)acrylate) and the ethoxylated and/or propoxylated derivatives thereof, bisphenol A di(meth)acrylate and the ethoxylated and/or propoxylated derivatives thereof.

The compositions of the invention may further contain at least one compound (C) that is different from (meth)acrylated compound (A) and compound (B).

Typically compositions of the invention comprise, relative to the total weight of the organic non-volatile content of the composition, at least 10% by weight of compounds (C). Typically this amount is at least 20%, more typically at least 30%, by weight. Typically this amount is at most 50%, more typically at most 70%, by weight.

Compounds (C) may be selected from one or more (meth) acrylated compounds that have a molecular weight (MW) of from 200 to 5,000 Daltons.

Compounds (C) typically have a molecular weight (MW), and more in particular a weight average molecular weight, of from 200 to 5,000 Daltons. Typically the MW of these compounds is at least 300 and more preferably at least 500 Daltons. Typically the MW of these compounds is at most 2,000 and more preferably at most 1,000 Daltons.

Compounds (C) typically are oligomers or polymers, more typically they are oligomers.

Preferably compounds (C) are selected from one or more of the following: polyester (meth)acrylates, urethane (meth) acrylates, alkoxylated (meth)acrylated oligomers, epoxy (meth)acrylates, aminated (meth)acrylates, (meth)acrylated (meth)acrylics, (meth)acrylic (co)polymers (also referred to as full acrylics) and inert polyesters that optionally are chlorinated.

Examples of suitable polyester (meth)acrylates are acrylated epoxidized soybean oil compounds like EBECRYL® 860 (Cytec), fatty acid containing polyester (meth)acrylates like EBECRYL® 870, EBECRYL® 657, EBECRYL® 450 (Cytec), and polyester (meth)acrylates like EBECRYL® 800, EBECRYL® 884, EBECRYL® 810 and EBECRYL® 830 (Cytec).

Examples of suitable epoxy (meth)acrylates are the di(meth)acrylate of diglycidyl ether of Bisphenol A (BADGED(M)A), and modifications thereof (see for instance EBECRYL® 3700 or EBECRYL® 600, EBECRYL® 3701, EBECRYL® 3703, EBECRYL® 3708 and EBECRYL® 3639 from Cytec).

Examples of suitable urethane (meth)acrylates are EBECRYL® 284, EBECRYL® 264, EBECRYL® 210, EBECRYL® 230, EBECRYL® 1290 (Cytec).

Examples of suitable aminated (meth)acrylates are EBECRYL® 80, EBECRYL® 81, EBECRYL® 83, EBECRYL® 7100, P115 and others.

Examples of suitable (meth)acrylic (co)polymers that may be used are EBECRYL® 745 and/or EBECRYL® 1200.

Examples of suitable inert polyesters include, but are not limited to EBECRYL® 525 and optionally chlorinated variants thereof (such as EBECRYL® 436 and others).

Compositions of the invention typically comprise at least one photoinitiator (D). Photoinitiators (D) where present typically are added in an amount of from 0.1 to 10%, by weight relative to the total weight of the organic non-volatile content of the composition. Examples of suitable photoinitiators include but are not limited to an aryl ketone type photoinitiator (such as an acetophenone, a benzophenone, an alkylaminobenzophenone, a benzyl, a benzoin, a benzoin ether, a benzoin dimethyl ketal, a benzoyl benzoate, 1-hydroxycyclohexyl phenyl ketone or an α-acyloxime ester), a sulfur-containing photopolymerization initiator (such as a sulfide or a thioxanthone), an acylphosphine oxide (such as an acyldiarylphosphine oxide) or other photopolymerization initiators. The photopolymerization initiator may be used as a mixture of at least two types thereof in combination. Further, the photopolymerization initiator may be used in combination with a photosensitizer such as an amine. The photoinitiator (D) can be a polymeric photoinitiator. Examples of suitable polymeric photoinitiators that may be used in the context of the present invention are P36, P39 and the like.

Alternatively or in addition, compositions of the invention may comprise at least one radical polymerization initiator such as benzoyl peroxide, methyl cyclohexanone peroxide, cumene hydroperoxide, diisopropyl benzene peroxide, di-t-butyl peroxide, t-butyl peroxide and the like.

The compositions according to the invention may also comprise a filler (E). When a filler (E) is used, it is typically present in an amount of at least 10% by weight, more preferably at least 30%, most preferably at least 50%. Typically this amount is at most 90%, more typically at most 80% by weight. These amounts are relative to the total weight of the organic non-volatile content of the composition.

Examples of materials suitable for use as fillers include, but are not limited to silica, zirconia, titania, ceria, alumina, antimony oxide, and mixtures thereof. Silica fillers are preferred. The filler may optionally comprise functional groups such as (meth)acrylate groups.

Preferred fillers (E) are nanoscale fillers (also called nanoparticules or nanoparticulate fillers) having a volume median diameter of from 1 to 999 nm, preferably from 1 to 100 nm as determined by dynamic light scattering. The volume median diameter of the nanoparticles may be determined typically by a known laser diffraction/scattering technique using, for example, a particle size analyzer (e.g., product name "Nanotrac UPA-EX150" (supplied by Nikkiso Co., Ltd.)). By volume median diameter is meant the diameter such that half the volume of the particles is contained in particles having a larger diameter and half is contained in particles having a smaller diameter.

Most preferred fillers (E) are silica nanoparticles. Some non-limitative examples of commercially available silica nanoparticles are known under the trade names NANOCRYL C146 (Hanse Chemie AG, neopentyl glycol propoxy diacrylate dispersion with a silica content of 50% by weight), NANOCRYL C150 (by Hanse Chemie AG, trimethylolpropane triacrylate dispersion with a silica content of 50% by weight), MEK-ST (Nissan Chemical Industries, Ltd., MEK dispersion with a solid content of 30% by weight), MEK-ST-L (Nissan Chemical Industries, Ltd., MEK dispersion with a solid content of 30% by weight), MEK-ST-UP (supplied by Nissan Chemical Industries, Ltd., MEK dispersion with a solid content of 20% by weight), MIBK-ST (supplied by Nissan Chemical Industries, Ltd., MIBK dispersion with a solid content of 30% by weight), MIBK-SD (supplied by Nissan Chemical Industries, Ltd., surface modified silica, MIBK dispersion with a solid content of 30% by weight), MIBK-SD-L (supplied by Nissan Chemical Industries, Ltd., surface-modified silica, MIBK dispersion with a solid content of 30% by weight), PL-3 (supplied by Fuso Chemical Co., Ltd., colloidal silica, MEK dispersion with a solid content of 20% by weight. Particularly preferred silica nanoparticles is MEK-ST.

The use of a filler (E) in a composition according to the present invention advantageously improves the scratch resistance and/or the abrasion resistance of the coating obtained from the composition.

In a first embodiment of the present invention, the compositions comprising a filler (E) comprise at least one acrylated compound (A). In a second embodiment, the compositions comprising a filler (E) comprise at least one (meth)acrylated compound (A) comprising the residue of at least one linking compound (b2) selected from polyisocyanates. In a third embodiment, the compositions comprising a filler (E) comprise at least one (meth)acrylated compound (A) prepared from a linking compound (b2) selected from epihalohydrins and acrylic acid as (meth)acrylating compound (c1). In a fourth embodiment, the compositions comprising a filler (E) comprise at least one (meth)acrylated compound (A) comprising the residue of at least one linking compound (b2) selected from epihalohydrins and the residue of at least one linking compound (b1). In a fifth embodiment, the compositions comprising a filler (E) comprise at least one (meth)acrylated compound (A) comprising the residue of at least one linking compound (b1).

The compositions according to the present invention comprising a filler (E) preferably comprise at least one acrylated compound (A).

In a particular embodiment of the invention, the composition is a coating composition. Coating compositions can be clear (e.g. lacquers or varnishes) or pigmented. Compositions of the invention in particular exhibited excellent adhesion on plastics, including polyvinylchloride, polycarbonate, polyethylene, acrylonitrile butadiene styrene copolymers, . . . etc. A preferred composition of the invention is a hard coat composition. It is preferably a hard coat composition for plastics. By a hard coat composition in the context of the invention is meant to designate a composition that after cure typically has a Persoz hardness of at least 150 sec as measured at 25° C. on 40 micron films on glass. Other methods used to characterize a coating hardness are the scratch resistance or the abrasion resistance as described below. A hard coat composition in the context of the invention is meant to designate a composition that after cure typically has a scratch resistance expressed in percentage of gloss retention of at least 90% and/or an abrasion resistance expressed as a difference of haze before and after test of at most 10.

In another particular embodiment of the invention the composition can be an ink or overprint varnish. The ink may be an ink used in lithographic, flexographic or inkjet applications. Inks of the invention may be used in the packaging industry, and are suitable for use on food packaging and more in particular for indirect food contact.

Compositions of the invention can also be an adhesive, they are further suited for the making of polymer matrices in composite materials. Compositions of the invention can also be used in stereolithography applications.

Substrates that may be treated or coated with compositions of the invention include metal, wood, paper, concrete, plastics (porous and non-porous), glass, as well as coating surfaces. Articles or materials to which the coating composition is applied may for instance already contain one or more coating layers (e.g. articles or material may already contain a primer or a base coat).

Compositions of the invention can be applied on a substrate via any suitable technique used in the art that includes but are not limited to brush coating, dip coating, roller coating, curtain coating, spray coating, vacuum coating, flexo printing, gravure printing, lithographic printing, inkjet printing etc.

Compositions of the invention typically have a viscosity at 25° C. in the range of from 400 to 150,000 mPa·s. More preferably the viscosity at this temperature is in the range of from 400 to 100,000 mPa·s, most preferably from 400 to 50,000 mPa·s.

Compositions of the invention can be cured by exposure to actinic radiations such as ultraviolet radiations, γ-rays, X-rays or by electron beam. They are typically cured by ultraviolet irradiation, generally in the presence of photoinitiator, which may be a polymeric photoinitiator. They can also be cured by electron-beam irradiation, allowing the use of compositions free of photoinitiator. The compositions according to the invention are providing rapid curing, comparable to state-of-the-art rapid curing formulations that do not contain any cyclic ether polyol.

Curing time and conditions may vary according to the constituents of the composition, the thickness of the coating film and the active energy ray source used. Usually curing is achieved by irradiation for about 0.1 to about 60 seconds. Further, for the purpose of completing the curing reaction, a heat treatment may be carried out after irradiation with active energy rays.

Though solvents may be used, compositions of the invention typically comprise at most 0.1% by weight of solvents. Usually this amount is at most 0.01% by weight, more preferably at most 0.001% by weight.

(Meth)acrylated compounds (A) of the invention typically are water-insoluble compounds. By "a water-insoluble compound" is meant to designate in the present invention that the compound is not self-emulsifiable or self-dispersible, but forms emulsions or dispersions in water or in aqueous solutions in the presence of a suitable external emulsifier. Typically such water-based compositions (emulsions or dispersions) would comprise at most 70% by weight of water. Usually this amount would be at most 65% by weight, more preferably at most 50% by weight.

Yet a further aspect of the invention concerns a coating composition, ink, overprint varnish, adhesive or composite matrix comprising at least one compound and/or at least one composition according to the invention. Provided are also coating compositions, inks, overprint varnishes, adhesives or composite matrixes prepared from at least one compound and/or at least one composition according to the invention.

Yet another aspect of the invention concerns an article or a substrate on which a composition of the invention is applied, usually on at least one of its surfaces. In particular there is provided an article or substrate that is coated, either entirely or partly with a composition of the invention. The coating composition can be a hard coat as described above.

Yet another aspect of the invention concerns a food packaging printed with an ink or an overprint varnish comprising at least one (meth)acrylated compound (A) according to the invention and/or at least one composition according to the invention. The food packaging in particular is one for indirect food contact.

Yet a further aspect of the invention concerns a composite matrix (clear or pigmented) comprising at least one (meth)acrylated compound (A) according to the invention and/or at least one composition according to the invention, and at least one reinforcement material. The reinforcement material used can be fibrous or non-fibrous. Examples of non-fibrous materials include but are not limited to alumina trihydrate, barium sulfate, calcium carbonate, clay, glass microspheres, kaolin, metal fillers, carbon black, mica, organic fillers (wood flour, corncobs, rice/peanut hulls, and nutshells), silicas, talc, wollastonite and other nano-sized materials. Examples of fibrous materials include but are not limited to boron fibers, carbon fibers, aramid fibers, ceramic fibers, glass fibers, natural (such as but not limited to hemp, jute, flax, kenaf, leaf fibers) or synthetic fibers as described in U.S. Pat. No. 8,012,573, EP2226171, U.S. Pat. No. 7,250,209. Often a glass filler is used as reinforcement material. Examples of suitable glass fillers include but are not limited to glass fibers, glass cloths, nonwoven glass fabrics and other glass fiber cloths, glass beads, glass flakes, glass powders, milled glass species and so forth. Among them, glass fibers, glass cloths and nonwoven glass fabrics are preferred in view of their being highly effective in reducing the coefficient of linear expansion. Glass cloths are most preferred.

Yet another aspect of the invention concerns a process for preparing a coated article or a coated substrate, comprising the steps of applying a coating composition of the invention on at least one of its surfaces, followed by radiation curing (e.g. via UV and/or electron beams). The coating composition can be a hard coat as described above.

The invention will now be described in more details in the examples below, which in no way are intended to be limited.

Throughout the invention and in particular in the examples the following measuring methods have been applied.

Epoxy value: the epoxy value is measured according to American Standard method (ASTM) D-1652. Results are reported in milliequivalent of epoxy functions per gram of product (meq/g).

Acid value: the acid value is measured according to American Standard method (ASTM) D 974-64 and is expressed in mg KOH/g of product.

Hydroxyl value (OH value): the hydroxyl value is measured according to ASTM E 222-73 and is expressed in mg KOH/g of product.

Isocyanate value (NCO value): the isocyanate value is measured according to ASTM D 2572-87 and is expressed in % NCO.

Lactide content: the residual lactide content is measured via $^1$H-NMR (Spectrometer: Bruker Avance 300) using CDCl3 as solvent. The mole % of free lactide vs polymerized lactide is determined by integration of the ring lactide methyl protons (doublet with chemical shift at δ 1.65) and the methyl groups the ring opened polymerized lactide (broadened doublets from δ 1.49 to 1.60).

Caprolactone content: The determination of the residual caprolactone content is done by gas chromatography and is expressed in weight % based on the total weight of the sample. The measurement is performed with a split/split less injection on a capillary column and using cyclohexyl acetate as an internal reference. Gas chromatograph: Hewlett Packard 6890 equipped with a split/split less injection system and an FID detector or equivalent. Column: Chrompack CP Sil 5CB-25 m-0.4 μm-0.32 mm. (Equivalent to HP-1 or OV-1).

Natural derived carbon content (% NDC): the natural derived carbon content is the percentage of natural derived carbon calculated on the total carbon content of the composition according to the following formula:

% NDC=100*amount of natural derived carbon/
(amount of natural derived carbon+petrochemical derived carbon)

Molecular weight (GPC): the number-average molecular weight (Mn), the weight-average molecular weight (Mw) and polydispersity are determined by conventional gel permeation chromatography (GPC) with polystyrene standards EasyCal from Polymer Laboratories (Molecular Weight range: 200-7,500,000 g/mol). A small portion of sample is dissolved in tetrahydrofuran (THF) and injected into a liquid chromatograph (Merck-Hitachi L7100) equipped with 4 PLGel Mixed-A polystyrene divinylbenzene GPC columns (300 mm×7.5 mm×20 μm). The components of the sample are separated by the GPC columns based on their molecular size in solution and detected by a Refractive Index detector. Data were gathered and processed by Polymer Laboratories Cirrus GPC software.

Viscosity: viscosity is measured with a rotational viscometer at 25° C. (unless otherwise specified) with defined shear rate of 20 s−1, according to DIN EN ISO 3219. The viscosity value is expressed in mPa·s Reactivity: the reactivity measurement consists in the evaluation of the minimum necessary UV-dose for curing the coating. A film of 10 μm is applied on paper and exposed to UV radiations from a 80 W/cm non focalized medium pressure mercury lamp at a defined conveyer speed. The conveyer speed is varied in order to determine the maximum conveyer speed to be used to obtain a fully cured film. The fully cured character is assessed by submitting the film to 50 double rubs with a wad of cotton drenched in acetone. A fully cured film is not visually affected by this test. The UV-dose (expressed in conveyer speed (m/min) necessary to pass the acetone double rubs test is referred to as the reactivity of the coating.

Criteria used in Tables 3-1 and 3-2:
A (Excellent): 50 m/min or more
B (Good): 30 m/min or more and less than 50 m/min
C (Fair): 10 m/min or more and less than 30 m/min
D (Poor): less than 10 m/min Glass transition temperature (Tg): Tg is measured according ASTM E1640-09 and is expressed in ° C. The conditions are as follows: DMA Q800 (TA instruments) tensile mode, frequency: 1 Hz, strain 10-30 tensile mode, frequency: 1 Hz, strain 10-30 μm, heating profile: −50 to 250° C. at 3°/min, sample dimension: 12×7.5×0.08 mm.

Young's modulus: Young's modulus is determined as the slope of the linear part of a stress-strain curve obtained for a free-standing film sample. The results are expressed in MPa. The formulated resin is casted on a release substrate and next cured 5 times at the maximum cure speed of the formulation on UV-conveyor belt. Measurement conditions of the tensile experiments: temperature: 23° C.; relative humidity: 50%; Zwick Z010 tensile testing machine; cross-head speed: 50 mm/min; rectangular samples with dimensions: 30 mm×10 mm×0.08 mm; number of test specimens: 3-5.

The hardness of the coatings is evaluated according to the 3 methods described below, hardness (Persoz), scratch resistance, abrasion resistance. Examples 5 to 7 and Comparative Examples 1 and 2 of the present invention make use of the Persoz test and Examples 12 to 19 and Comparative Examples 4 and 5 make use of the scratch and abrasion resistance tests.

Hardness (Persoz): pendulum hardness is measured for a 40 μm film on glass, cured 2× with the minimal cure dose, and is measured as the time in seconds required for the amplitude of the pendulum to drop from 12° to 4°. Harder coatings result in a longer oscillation time (less damping effect).

Scratch Resistance: A 60-degree gloss of the coated surface of a sample before testing was measured with a gloss meter, and the coated surface was rubbed through 100-times reciprocating movements of a #0000 steel wool under a load of 1 kg/cm². After the testing, the gloss of the rubbed portion was measured in the same manner as that before testing, a gloss retention was determined by calculation according to the following equation, the calculated gloss retention was evaluated according to the following criteria. The results are indicated as "Scratch resistance" in Tables 3-1 and 3-2.

Gloss retention %=(Gloss after testing)/(Gloss before testing)×100

Criteria:
 A (Excellent): 95% or more
 B (Good): 90% or more and less than 95%
 C (Fair): 80% or more and less than 90%
 D (Poor): less than 80%

Abrasion Resistance: The hazes of the coated surface of a sample were measured with a hazemeter before and after testing using a Taber Abrader, and the difference in haze (Δhaze) between before and after testing was evaluated according to the criteria mentioned below, and the results are indicated as "Abrasion resistance" in Tables 3-1 and 3-2. A truck wheel (abrading wheel) used in testing is the product name "CS-10F" (supplied by TABER Industries) and was rotated 100 times under a load of 500 g at a rate of 60 revolutions per 1 minute.

Criteria:
 A (Excellent): less than 5
 B (Good): 5 or more and less than 10
 C (Fair): 10 or more and less than 15
 D (Poor): 15 or more Impact Resistance: A ¼-inch impact head (500 g load) was dropped on the coated surface of a sample, the height at the highest position of the impact head at which the coating does not break was measured using a Du Pon't type impact tester, and the impact resistance was evaluated according to the following criteria.

Criteria:
 A (Excellent): 40 cm or more
 B (Good): 30 cm or more and less than 40 cm
 C (Fair): 20 cm or more and less than 30 cm
 D (Poor): less than 20 cm Accelerated Weathering Resistance: A sample with a coated surface was subjected to accelerated weathering testing using the Xenon Weather-Ometer, and 1500 hours into the testing, the surface was observed, and the accelerated weathering resistance was evaluated according to the following criteria.

Criteria:
 A (Excellent): no change
 B (Good): no cracking, but slightly lowered gloss
 C (Fair): no cracking, but apparently lowered gloss
 D (Poor): cracking in overall surface Dynamic light scattering: The volume median diameter of the filler may be determined typically by a known laser diffraction/scattering technique using, for example, a particle size analyzer (e.g., product name "Nanotrac UPA-EX150" (supplied by Nikkiso Co., Ltd.)). By volume median diameter is meant the diameter such that half the volume of the particles is contained in particles having a larger diameter and half is contained in particles having a smaller diameter.

Example 1

In a 3-neck reactor equipped with a Dean-Stark Column 352 gr of isosorbide (Polysorb P from Roquette) and 2200 gr of epichlorohydrin are charged and heated to 115° C. During 10 hrs, 400 gr of a 50% NaOH aqueous solution is fed into the reactor while the water/epichlorohydrin mixture is continuously distilled. After separation the epichlorohydrin is sent back into the reactor. When all the water is removed at the end of the caustic solution feed, the reaction mixture is distilled at 150° C. under reduced pressure to remove the excess of epichlorohydrin. Then, 600 gr acetone are added and the NaCl salt is removed by filtration. The epoxy resin is distilled again at 150° C. to remove the acetone. About 525 gr of an epoxy resin is obtained with an epoxy value of 4.5 meq/g.

For the acrylation 0.25 gr of a chromium catalyst (Hycat AO) is added to the reactor. At 95° C. a mixture of 205 gr of acrylic acid, 0.8 gr of chromium catalyst and 0.5 gr of hydroquinone is fed to the epoxy resin over a period of about 1 hr. The reaction is continued till an acid value below 5 mg KOH/g is reached and an epoxy value below 0.1 meq/g. The resin is further diluted with TPGDA to obtain a composition with 70 wt % of resin.

Example 2

145 gr of isosorbide (Posysorb P from Roquette), 360 gr of lactide L (Puralact L from Purac), 0.5 gr of stannous octoate, 0.5 gr of tripenylphosphite and 0.25 gr of hydroquinone monomethylether (MEHQ) are charged into a double-wall glass reactor equipped with a stirrer, a thermocouple attached to a thermoregulator, a gas inlet tube, a connection to vacuum and an distillation column. The temperature is raised to 140° C. and kept at this temperature till the free lactide content is less than 3 mole %.

The mixture is cooled by adding 356 gr of toluene, 156 gr of acrylic acid, 20 gr of methanesulphonic acid (70 wt % in water), 0.15 gr of copper oxide, 0.8 gr of MEHQ. The mixture is heated to 120° C. until no more water is distilled over. The mixture then is cooled down to 60° C. and another 185 gr of toluene are added. The mixture is washed three times with 150 gr water and dried by means of an azeotropic distillation. Subsequently the toluene is distilled off under reduced pressure of about 30 mm Hg and the reaction product is filtered. The polyester-acrylate thus obtained has a yellowish color and a viscosity of 6000 mPa·s at 25° C. after dilution with 30 wt % TPGDA.

Example 3

130 gr of isosorbide (Posysorb P from Roquette), 520 gr of ε-caprolactone, 0.3 gr of phosphoric acid (85 wt % in water) are charged into a double-wall glass reactor equipped with a stirrer, a thermocouple attached to a thermoregulator, a gas inlet tube, a connection to vacuum and an distillation column. The temperature is raised to 140° C. and kept at this temperature till the free caprolactone content is less than 1 wt %.

The mixture is cooled by adding 420 gr of toluene, 131 gr of acrylic acid, 18 gr of methanesulphonic acid (70 wt % in water), 0.1 gr of copper oxide, 0.7 gr of MEHQ. The mixture is heated to 120° C. until no more water is distilled over. The mixture then is cooled down to 60° C. and another 310 gr of toluene are added. The mixture is washed three times with 150 gr water and dried by means of an azeotropic distillation. Subsequently the toluene is distilled off under reduced pressure of about 30 mm Hg and the reaction product is filtered. The polyester-acrylate thus obtained has a yellowish color and a viscosity of 800 mPa·s at 25° C.

Example 4

A polyester polyol is synthesized as follows:
 45 gr of isosorbide (Posysorb P from Roquette), 180 gr of ε-caprolactone, 0.1 gr of phosphoric acid (85 wt % in water)

are charged to a double-wall glass reactor equipped with a stirrer, a thermocouple attached to a thermoregulator, a gas inlet tube, a connection to vacuum and an distillation column. The temperature is raised to 140° C. and kept at this temperature till the free caprolactone content is less than 1%.

The polyester obtained has an OH value of 147 mg KOH/g
The urethane acrylate is made as follows:
To the above polyester are charged: 130 gr of isophorone diisocyanate (IPDI), 0.13 gr of dibutyl tin dilaurate (DBTL) and the mixture is heated to 50° C. After the exothermic reaction and at a NCO value of 7%, a mixture of 67 gr of hydroxyethylacrylate (HEA) and 0.13 gr of MEHQ is added over 1 hr. The reaction is continued at 80° C. till the NCO value has reached 0.2%. An additional amount of 105 gr HDDA is added while the mixture is cooled.

The resin has a viscosity of 34000 mPa·s at 25° C.

Example 20

100 gr of isosorbide (Polysorb P from Roquette), 238.5 gr TDI (toluene diisocyanate), 213 gr TPGDA, 0.5 gr BHT and 0.12 gr DBTL is charged into a double-wall glass reactor equipped with a stirrer and a thermocouple, attached to a thermoregulator. The mixture is slowly heated to 50° C. to start the reaction. When an NCO value of 4.0 meq/g is reached, the temperature is raised to 65° C. and 159 gr HEA is fed over 2 hr.

The reaction is continued at 80° C. till the NCO value has reached 0.2%.

The resin has a viscosity of 100000 mPa·s at 60° C.

Table 1 summarizes the major components and their amounts used in Examples 1 to 4 as well as some of their characteristics. Two comparative resins (EBECRYL 605 and EBECRYL 284) are also described in table 1. They are standard UV curable resins that do not contain any cyclic ether polyol. EBECRYL 605 is a bisphenol A based epoxy acrylate diluted in tripropyleneglycol diacrylate (TPGDA). It is not based on any renewable raw material and it typically provides high hardness and cure speed to a composition. EBECRYL 284 is a caprolactone based urethane acrylate diluted in hexanediol diacrylate (HDDA). It is also not based on any renewable raw material.

TABLE 1

| | Ex. 1 | Ex. 2 | Ex. 3 | Ex. 4 | Ex. 20 | EB 605 | EB 284 |
|---|---|---|---|---|---|---|---|
| Resin (wt %) made of: | 70 | 70 | 100 | 80 | 70 | 75 | 85 |
| Isosorbide (mol %) | 20 | 19 | 12.5 | 10 | 20 | | |
| Epichlorohydrin (mol %) | 40 | | | | | | |
| ε-caprolactone (mol %) | | | 62.5 | 50 | | | |
| lactide (mol %) | | 45 | | | | | |
| IPDI (mol %) | | | | 20 | | | |
| TDI | | | | | 40 | | |
| HEA (mol %) | | | | 20 | 40 | | |
| Acrylic acid (mol %) | 40 | 36 | 25 | | | | |
| Dilution | | | | | | | |
| HDDA (wt %) | | | | 20 | | | 15 |
| TPGDA (wt %) | 30 | 30 | | | 30 | 25 | |
| Viscosity (25° C., mPa · s) | 8500 | 6000 | 800 | 34000 | 100000 | 7000 | 56000 |
| MW[1] of the undiluted resins formed | 400 | 600 | 750 | 1300 | 720 | 520 | 1200 |

TABLE 1-continued

| | Ex. 1 | Ex. 2 | Ex. 3 | Ex. 4 | Ex. 20 | EB 605 | EB 284 |
|---|---|---|---|---|---|---|---|
| % NDC (Diluent not included) | 33 | 78[2] | 14 | 8.5 | 18 | 0 | 0 |

[1]theoretical MW
[2] both the lactide and isosorbide are bioderived

Examples 5 to 7 and Comparative Examples 1 and 2

The resins of Examples 1, 2 and 4 and EBECRYL 605, EBECRYL 284 are formulated as described in Table 2. The formulations are evaluated for reactivity, hardness, Tg and Young modulus according to the methods described supra. The results of the measurements are summarized in Table 2.

TABLE 2

| parts | Ex. 5 | Ex. 6 | Ex. 7 | C. Ex. 1 | C. Ex. 2 |
|---|---|---|---|---|---|
| Undiluted resin of Ex. 1 | 70 | | | | |
| Undiluted resin of Ex. 2 | | 70 | | | |
| Undiluted resin of Ex. 4 | | | 60 | | |
| Undiluted EB 605 | | | | 75 | |
| Undiluted EB 284 | | | | | 64 |
| TPGDA | 30 | 30 | 20 | 25 | 20 |
| HDDA | | | 15 | | 11 |
| Additol BCPK | 5 | 5 | 5 | 5 | 5 |
| Reactivity (m/min) | >50 | 25 | 10 | 25 | 10 |
| Hardness (sec) | 173 | 191 | 184 | 225 | 178 |
| Tg (° C.) | 70 | 61 | 65 | 85 | 54 |
| Young modulus (MPa) | 1206 | 1610 | 425 | 1651 | 288 |

The evaluation results in Table 2 show that the compositions comprising (meth)acrylated compounds (A) according to the present invention have a reactivity similar or higher than state-of-the-art fast curing compositions that do not contain any cyclic ether polyol. They also exhibit similar or higher Tg and hardness what make them advantageous for hard coat applications. Particularly, Example 5 shows an extremely high reactivity when compared to Comparative Example 1 together with close hardness and Tg. Example 7 in comparison to Comparative Example 2 has a similar reactivity and slightly higher hardness and Tg.

Example 8

84 gr of isosorbide (Posysorb P from Roquette), 255 gr of isophorone diisocyanate (IPDI), 0.08 gr dibutyl tin dilaurate (DBTDL) and 200 gr of methyl ethyl ketone (MEK) are charged into a double-wall glass reactor equipped with a stirrer and a thermocouple attached to a thermoregulator. The mixture is heated to 50° C. After the exothermic reaction and at a NCO value of 9%, a mixture of 67 gr of hydroxyethylacrylate (HEA), 394 gr of pentaerythritol triacrylate "PETIA" (mixture of tri- and tetra-acrylate) and 0.64 gr of hydroquinone monomethylether (MEHQ) are added over 1 hr. The reaction is continued at 70° C. till the NCO value has reached below 0.1%. The urethane acrylate 1 (UA1) is obtained.

Example 9

79 gr of isosorbide (Posysorb P from Roquette), 240 gr of isophorone diisocyanate (IPDI), 0.08 gr dibutyl tin dilaurate (DBTDL) and 200 gr of methyl ethyl ketone (MEK) are charged into a double-wall glass reactor equipped with a stirrer and a thermocouple attached to a thermoregulator. The mixture is heated to 50° C. After the exothermic reaction and at a NCO value of 9%, a mixture of 481 gr of pentaerythritol triacrylate "PETIA" (mixture of tri- and tetra-acrylate) and 0.64 gr of hydroquinone monomethylether (MEHQ) are added over 1 hr. The reaction is continued at 70° C. till the NCO value has reached below 0.1%. The urethane acrylate 2 (UA2) is obtained.

Example 10

38 gr of isosorbide (Posysorb P from Roquette), 294 gr of hexane diisocyanate isocyanurate, 0.08 gr dibutyl tin dilaurate (DBTDL) and 200 gr of methyl ethyl ketone (MEK) are charged into a double-wall glass reactor equipped with a stirrer and a thermocouple attached to a thermoregulator. The mixture is heated to 50° C. After the exothermic reaction and at a NCO value of 8%, a mixture of 468 gr of pentaerythritol triacrylate "PETIA" (mixture of tri- and tetra-acrylate) and 0.64 gr of hydroquinone monomethylether (MEHQ) are added over 1 hr. The reaction is continued at 70° C. till the NCO value has reached below 0.1%. The urethane acrylate 3 (UA3) is obtained.

Example 11

67 gr of isosorbide (Posysorb P from Roquette), 518 gr of hexane diisocyanate isocyanurate, 0.08 gr dibutyl tin dilaurate (DBTDL) and 200 gr of methyl ethyl ketone (MEK) are charged into a double-wall glass reactor equipped with a stirrer and a thermocouple attached to a thermoregulator. The mixture is heated to 50° C. After the exothermic reaction and at a NCO value of 10%, a mixture 215 gr of hydroxyethylacrylate (HEA) and 0.64 gr of hydroquinone monomethylether (MEHQ) are added over 1 hr. The reaction is continued at 70° C. till the NCO value has reached below 0.1%. The urethane acrylate 4 (UA4) is obtained.

Comparative Example 3

162 gr of polyethyleneglycol (PEG600, MW 600), 452 gr of hexane diisocyanate isocyanurate, 0.08 gr dibutyl tin dilaurate (DBTDL) and 200 gr of methyl ethyl ketone (MEK) are charged into a double-wall glass reactor equipped with a stirrer and a thermocouple attached to a thermoregulator. The mixture is heated to 50° C. After the exothermic reaction and at a NCO value of 8%, a mixture 187 gr of hydroxyethylacrylate (HEA) and 0.64 gr of hydroquinone monomethylether (MEHQ) are added over 1 hr. The reaction is continued at 70° C. till the NCO value has reached below 0.1%. The Comparative urethane acrylate (C. Ex. 3) is obtained.

Examples 12-15 and Comparative Example 4

The resins of Examples 8 to 11 and Comparative Example 3 are formulated and evaluated as described in Table 3-1.

The samples used to evaluate scratch, abrasion, impact and accelerated weathering resistance are prepared as follows. Coated panels each having a coating thickness of from 8 to 10 μm are prepared by applying each composition to a 2-mm thick polycarbonate panel (supplied by Nippon Testpanel Co., Ltd.) using a bar coater No. 12, drying the coated layer in an oven at 80° C. for 5 minutes, curing the dried layer through irradiation using a UV irradiator (EYE INVERTOR GRANDAGE ECS-401GX supplied by Eye Graphics Co., Ltd.) at a peak irradiance of 400 mW/cm$^2$ and an integrated light quantity of 860 mJ/cm$^2$.

TABLE 3-1

|  | Ex. 12 | Ex. 13 | Ex. 14 | Ex. 15 | C. Ex. 4 |
|---|---|---|---|---|---|
| UA1 of Ex. 8 | 100 | | | | |
| UA2 of Ex. 9 | | 100 | | | |
| UA3 of Ex. 10 | | | 100 | | |
| UA4 of Ex. 11 | | | | 100 | |
| C. Ex. 3 | | | | | 100 |
| Photointiator [1] | 2.4 | 2.4 | 2.4 | 2.4 | 2.4 |
| Scratch resistance | B | B | A | B | C |
| Abrasion resistance | B | B | A | B | C |
| Impact resistance | A | A | B | A | D |
| Accelerated weathering resistance | A | A | B | A | D |
| Reactivity | B | B | A | B | D |

[1] 1-hydroxycyclohexyl phenyl ketone

The evaluation results in Table 3-1 show that the compositions according to the present invention have better performances in terms of scratch resistance, abrasion resistance, impact resistance, accelerated weathering resistance and reactivity than an urethane acrylate that does not contain any cyclic ether polyol. More particularly, the composition of Example 15 has better performances than the composition of Comparative Example 4.

Examples 16 to 19 and Comparative Example 5

The resins of Examples 8 to 11 and Comparative Example 3 are formulated and evaluated as described in Table 3-2.

TABLE 3-2

|  | Ex. 16 | Ex. 17 | Ex. 18 | Ex. 19 | C. Ex. 5 |
|---|---|---|---|---|---|
| UA1 of Ex. 8 | 100 | | | | |
| UA2 of Ex. 9 | | 100 | | | |
| UA3 of Ex. 10 | | | 100 | | |
| UA4 of Ex. 11 | | | | 100 | |
| C. Ex. 3 | | | | | 100 |
| MEK-ST (silica content 30%) [1] | 530 | 530 | 530 | 530 | 530 |
| Photointiator [2] | 2.4 | 2.4 | 2.4 | 2.4 | 2.4 |
| Scratch resistance | A | A | A | A | B |
| Abrasion resistance | A | A | A | A | B |
| Impact resistance | A | A | B | A | D |
| Accelerated weathering resistance | A | A | B | A | D |
| Reactivity | B | B | A | B | D |

[2] 1-hydroxycyclohexyl phenyl ketone
[1] MEK-ST: Dispersion of microparticulate silica having a volume median diameter of 10 to 20 nm in methyl ethyl ketone (trade name MEK-ST ® supplied by Nissan Chemical Industries, Ltd.)

The addition of silica to the compositions leads to increased performances in scratch and abrasion resistances of the coatings including in Comparative Example 5. Furthermore, the compositions comprising (meth)acrylated compounds (A) according to the present invention still have better performances in terms of scratch resistance, abrasion resistance, impact resistance, accelerated weathering resistance and reactivity than an urethane acrylate that does not contain any cyclic ether polyol. More particularly, the composition of Example 19 has better performances than the composition of Comparative Example 5.

Hence, (meth)acrylated compounds (A) according to the invention containing a cyclic ether polyol that can be obtained from renewable feedstocks are a possible and sustainable replacement of state-of-the-art petrochemical derived resins.

The invention claimed is:

1. A (meth)acrylated compound (A) prepared from
(a) at least one cyclic ether polyol,
(b) at least one linking compound (b1) and/or (b2), wherein the linking compound
   (b1) is selected from cyclic compounds (b11) containing at least one

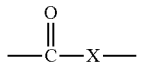

group in the cycle where X=O or NH, from hydroxy acids (b12) and/or from alkylene oxides (b13) containing from 2 to 4 carbon atoms and the linking compound (b2) is selected from epihalohydrins or polyisocyanates,
(c) a (meth)acrylating compound,
wherein if both compounds (b1) and (b2) are being used, compound (b1) forms a moiety that links the cyclic ether polyol (a) to the linking compound (b2) which attaches to the (meth)acrylating compound (c),
wherein at least one compound (b2) is being used, if a compound (b13) is being used, and
wherein the amounts of compounds (a), (b), and (c) sum up to 100%.

2. The compound according to claim 1, wherein the cyclic ether polyol is selected from dianhydrohexitols.

3. The compound according to claim 1, wherein the cyclic ether polyol is isosorbide.

4. The compound according to claim 1, wherein the linking compound (b11) is selected from lactones, lactides, lactams and mixtures thereof.

5. The compound according claim 1, wherein the linking compound (b12) is glycolic acid.

6. The compound according claim 1, wherein the linking compound (b13) is selected from ethylene oxide, propylene oxide and mixtures thereof.

7. The compound according to claim 1, wherein the epihalohydrin is epichlorhydrin.

8. The compound according to claim 1, wherein the polyisocyanate is selected from aliphatic polyisocyanates.

9. The compound according to claim 1, wherein the (meth)acrylating compound (c) is selected from an unsaturated acid, an acyl halide of the unsaturated acid, a corresponding anhydride of the unsaturated acid, a $C_1$-$C_4$ alkyl ester of the unsaturated acid (c1), or from compounds containing at least one reactive group capable to react with isocyanate groups as well as at least one (meth)acryloyl group (c2).

10. The compound according to claim 9, wherein the (meth)acrylating compound (c1) is selected from acrylic acid, methacrylic acid and mixtures thereof.

11. The compound according to claim 9, wherein the (meth)acrylating compound (c2) is selected from hydroxyethylacrylate, glycerol diacrylate, trimethylolpropane diacrylate and mixtures thereof.

12. The (meth)acrylated compound (A) according to claim 1 prepared from:
(a) at least one cyclic ether polyol,
(b) at least one linking compound (b2) selected from epihalohydrins or polyisocyanates and optionally at least one linking compound (b1) selected from cyclic compounds (b11) containing at least one

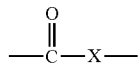

group in the cycle where X=O or NH, from hydroxy acids (b12) and/or from alkylene oxides (b13) containing from 2 to 4 carbon atoms,
(c) a (at least one) (meth)acrylating compound,
wherein if both compounds (b1) and (b2) are being used, compound (b1) forms a moiety that links the cyclic ether polyol (a) to the linking compound (b2) which attaches to the (meth)acrylating compound (c).

13. The (meth)acrylated compound (A) according to claim 1 prepared from:
(a) at least one cyclic ether polyol,
(b) at least one aliphatic linking compound (b1) selected from cyclic compounds (b11) containing at least one

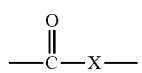

group in the cycle where X=O or NH, from hydroxy acids (b12) and/or from alkylene oxides (b13) containing from 2 to 4 carbon atoms and optionally at least one linking compound (b2) selected from epihalohydrins or polyisocyanates,
(c) a (at least one) (meth)acrylating compound wherein if both compounds (b1) and (b2) are being used, compound (b1) forms a moiety that links the cyclic ether polyol (a) to the linking compound (b2) which attaches to the (meth)acrylating compound (c), and
wherein at least one compound (b2) is being used, if a compound (b13) is being used.

14. A radiation curable composition comprising
at least 5% by weight relative to the total weight of the organic non-volatile content of the composition of at least one (meth)acrylated compound (A) according to claim 1,
optionally a reactive diluting monomer (B),
optionally at least one compound (C) selected from polyester (meth)acrylates, urethane (meth)acrylates, alkoxylated (meth)acrylated oligomers, epoxy (meth)acrylates, aminated (meth)acrylates, (meth)acrylated (meth) acrylics, (meth)acrylic (co)polymers and inert polyesters that optionally are chlorinated, and
optionally at least one photoinitiator (D).

15. The radiation curable composition according to claim 14 further comprising a nanoscale filler (E).

16. The radiation curable composition according to claim 15, wherein the nanoscale filler (E) is selected from silica, zirconia, titania, ceria, alumina, antimony oxide and is present in an amount of at least 10% by weight relative to the total weight of the organic non-volatile content of the composition.

17. The radiation curable composition according to claim 15, wherein the filler (E) is a nanoparticulate silica having a volume median diameter of from 1 to 100 nm.

18. The radiation curable composition according to claim 14 which is a coating, an ink, or an overprint varnish.

19. An article or substrate, having applied to at least part of one of its surfaces a composition of claim 14.

20. The radiation curable composition according to claim 14 comprising at least one photoinitiator (D).

21. The radiation curable composition according to claim 14 comprising at least one compound (C) selected from polyester (meth)acrylates, urethane (meth)acrylates, alkoxylated (meth)acrylated oligomers, epoxy (meth)acrylates, aminated (meth)acrylates, (meth)acrylated (meth)acrylics, (meth)acrylic (co)polymers and inert polyesters that optionally are chlorinated.

* * * * *